United States Patent [19]

Takahama et al.

[11] 4,223,550
[45] Sep. 23, 1980

[54] CARBON MONOXIDE DETECTING APPARATUS

[75] Inventors: Teizo Takahama; Toyoki Kazama; Tatumi Hieda, all of Kawasaki, Japan

[73] Assignee: Fuji Electric Co., Ltd., Kawasaki, Japan

[21] Appl. No.: 928,031

[22] Filed: Jul. 25, 1978

[30] Foreign Application Priority Data

Jul. 26, 1977 [JP] Japan .................................. 52-89408

[51] Int. Cl.$^2$ ............................................. G01N 27/04
[52] U.S. Cl. ............................................. 73/23; 422/98
[58] Field of Search ................... 73/23, 27 R; 338/34; 340/634; 23/232 E; 422/98

[56] References Cited

U.S. PATENT DOCUMENTS

| | | | |
|---|---|---|---|
| 3,479,257 | 11/1969 | Shaver | 23/232 E |
| 3,676,820 | 7/1972 | Taguchi | 73/27 R |
| 3,901,067 | 8/1975 | Boardman, Jr. et al. | 338/34 |
| 3,955,929 | 5/1976 | Kawakami et al. | 73/27 R |
| 4,000,089 | 12/1976 | Senda | 73/27 R |
| 4,121,548 | 10/1978 | Hattori et al. | 73/23 |

*Primary Examiner*—Stephen A. Kreitman
*Attorney, Agent, or Firm*—Sughrue, Rothwell, Mion, Zinn and Macpeak

[57] ABSTRACT

A carbon monoxide detecting apparatus is provided which is substantially unaffected by other coexisting gases in the gas atmosphere being sampled. The present invention includes a first carbon monoxide detecting element, a second carbon monoxide detecting element, and a comparing means. The first carbon monoxide detecting element is responsive to carbon monoxide gas and produces a stepwise change in a first film current over a first preselected range of carbon monoxide gas concentration. The second carbon monoxide detecting element is responsive to carbon monoxide gas and produces a stepwise change in a second film current over a second preselected range of carbon monoxide gas. The comparing means is responsive to the first and second film currents and provides an output difference signal $\Delta E$. The amplitude of the output difference signal $\Delta E$ is in accordance with the absolute value difference between the first film current and the second film current. The two preselected ranges of carbon monoxide gas concentration can be achieved by appropriately altering the structure of the respective carbon monoxide detecting element and/or by making the substrate temperatures of the two carbon monoxide detecting elements different.

6 Claims, 11 Drawing Figures

CARBON MONOXIDE DETECTING APPARATUS

BACKGROUND OF THE INVENTION

The present invention relates generally to carbon monoxide detecting apparatus, and more particularly, to a carbon monoxide detecting apparatus having a carbon monoxide detection response which is substantially unaffected by other coexisting gases in the gas atmosphere being sampled.

Gas detection apparatuses for detecting specific gases in a gas atmosphere have received considerable interest in recent years, primarily because of increased public concern for health and safety. An example of a detecting device for carbon dioxide is disclosed in U.S. Pat. No. 3,479,257.

Present gas detecting devices for carbon monoxide, however, are substantially affected by other coexisting gases in the gas atmosphere being sampled, and, thus, make it difficult to determine when a preselected carbon monoxide concentration level has been met or exceeded.

SUMMARY OF THE INVENTION

According to the present invention, a carbon monoxide detecting apparatus is provided which is substantially unaffected by other coexisting gases in the gas atmosphere being sampled. The present invention includes a first carbon monoxide detecting element, a second carbon monoxide detecting element, and a comparing means. The first carbon monoxide detecting element is responsive to carbon monoxide gas and produces a stepwise change in a first film current over a first preselected range of carbon monoxide gas concentration. The second carbon monoxide detecting element is responsive to carbon monoxide gas and produces a stepwise change in a second film current over a second preselected range of carbon monoxide gas. The comparing means is responsive to the first and second film currents and provides an output difference signal $\Delta E$. The amplitude of the output difference signal $\Delta E$ is in accordance with the absolute value difference between the first film current and the second film current. The two preselected ranges of carbon monoxide gas concentration can be achieved by appropriately altering the structure of the respective carbon monoxide detecting element and/or by making the substrate temperatures of the two carbon monoxide detecting elements different.

DETAILED DESCRIPTION OF THE PREFERRED EMBODIMENTS

The present invention utilizes wafer-type carbon monoxide detecting elements made from semiconductor materials. Each wafer-type carbon monoxide detecting exhibits a stepwise change in film current over a preselected range in carbon monoxide concentration. Copending application Ser. No. 924,324 filed July 13, 1978, corresponding to Japanese Patent Application Nos. 52-85917 and 52-85918, and assigned to the assignee of the present application, discloses a wafer-type carbon monoxide detecting element as employed in the present invention, the disclosure of which is incorporated by reference herein.

Figure 1B:
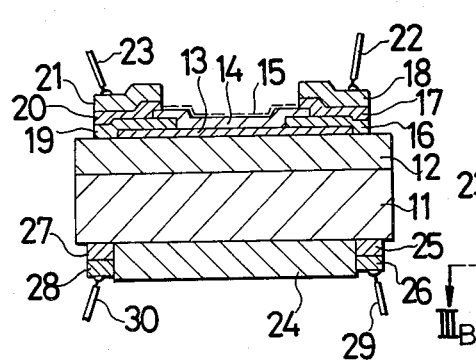
FIG. 1B shows a cross-sectional view of the carbon monoxide detecting element taken along line I—I of FIG. 1A.
Figure 1A:
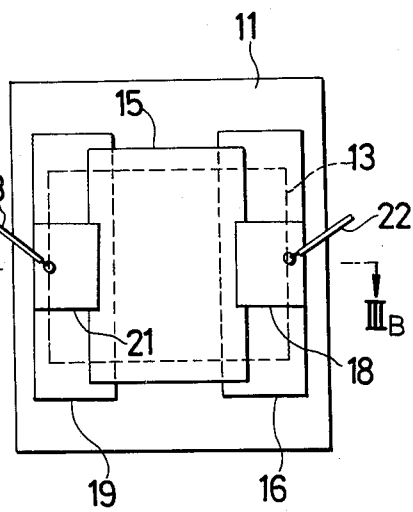
FIG. 1A shows a top plan view of a carbon monoxide detecting element as employed by the carbon monoxide detecting apparatus of the present invention.

FIGS. 1A and 1B show a top plan view and a cross-sectional view, respectively, of a carbon monoxide detecting element as employed in the present invention. Reference numeral 11 designates a substrate made of, for example, silicon (Si). An insulating film 12 of silicon oxide ($SiO_2$) is formed on a first surface of substrate 11. A first film 13 is formed on the insulating film 12. First film 13 predominantly comprises stannic oxide, and has a donor selected from the group consisting of antimony (Sb) and bismuth (B). An intermediate film 14 is formed on the first film 13. Intermediate film 14 predominantly comprises stannic oxide and has an acceptor selected from the group consisting of platinum (Pt), aluminum (Al) and boron (B). A second film 15 predominantly of platinum is formed on the intermediate film 14. Alternately, second film 15 can be modified so as to have gold (Au) incorporated therein. The second film 15 is so formed on the intermediate film 14 that the second film 15 is of an average thickness of 0.3 to 30.0 platinum atom layers and does not exhibit a metallic, electrical conductivity because of the small thickness, as is well known in the art.

Films 13, 14 and 15 are formed, for example, in accordance with the high-frequency reactive sputtering method. In manufacturing films 13 and 14, a tin target is made, and a plurality of minute and thin pieces of antimony or platinum are placed on the tin target. It follows that the quantity of the impurity such as antimony or platinum added to the stannic oxide is adjusted by changing the area occupied by the thin impurity pieces with respect to the entire area of the tin target. In comparison, in manufacturing film 15, the target is made of platinum. In this case, platinum makes up the target, and the quantity of gold with respect to platinum in film 15 can be adjusted by changing the area occupied by the thin pieces of gold with respect to the entire area of the platinum target.

A pair of first electrodes 16 and 19 are formed on the insulating film 12. The pair of respective electrodes 16 and 19 are partly interposed between the first film 13 and the intermediate film 14. A pair of second electrodes 17 and 20 are provided on first electrodes 16 and 19, respectively, and a part of each second electrode overlaps film 14. Films 18 and 21 of gold are formed on electrodes 17 and 20 to connect lead wires 22 and 23 to the electrodes 17 and 20, respectively.

Substrate 11 serves both as substrate and as a heating resistor for heating the carbon monoxide detecting device. For this second purpose, heating electrodes 25 and 27 are provided on the second surface of the substrate 11, and are connected to heating lead wires 29 and 30 through films 26 and 28 of gold, respectively. A film 24 is provided between heating electrodes 25 and 27 and acts as an insulating surface protecting film in a manner similar to that of film 12. It should be noted, however, that film 24 may be omitted.

The thickness of various elements of the carbon monoxide detecting element, as shown in FIGS. 1A and 1B, are given by way of example, in Table 1 below.

TABLE 1

| Substrate 11 | 200 μm |
|---|---|
| Insulating Layer 12 | 0.7 μm |
| First Film 13 | 0.06 μm |
| Intermediate Film 14 | 0.07–0.15 μm |
| Second Film 15 (unmodified and modified) | Average 0.000012–0.012 μm |
| First Electrodes 16, 19 | 0.2 μm |
| Second Electrodes 17, 20 | 0.2 μm |

Figure 2:
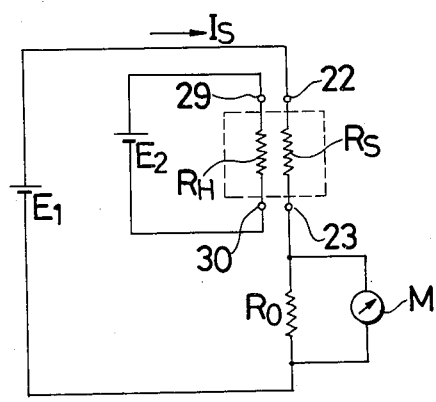
FIG. 2 shows a schematic circuit diagram of an experimental circuit utilizing the carbon monoxide detecting element as employed by the carbon monoxide detecting apparatus of the present invention.

Shown in FIG. 2 is an experimental circuit which utilizes the carbon monoxide detecting element in employing the present invention. In this circuit, reference character $E_1$ designates a driving power supply for operating the carbon monoxide detecting element. The voltage of the power supply $E_1$ is, for example, approximately 1 V. The driving power supply $E_1$ is connected to lead wires 22 and 23 through a current detecting resistor $R_O$. A heating power supply $E_2$ is provided to heat the carbon monoxide detecting element, and its voltage is set, for example, to about 4 V. The heating power supply $E_2$ is connected to the lead wires 29 and 30. The resistor $R_O$ is a fixed resistor of, for example, 1 ohm, and a volt meter M is connected in parallel between the two terminals of resistor $R_O$. Reference character $R_S$ designates the resistance of the films between lead wires 22 and 23. Reference character $I_S$ designates a film current flowing in that film. Reference character $R_H$ designates a heating resistance between lead wires 29 and 30. In the experimental result described below, the film resistance $R_S$, and the film current $I_S$ were calculated using the voltage readings obtained on volmeter M. It should be noted that the heating temperature of the substrate 11 can be varied by varying the voltage provided by power supply $E_2$.

In the first experiment, the quantity of gold in second film 15 was varied while the quantity of platinum was maintained constant. In the first experiment, the ambient temperature was 25° C., the ambient humidity was 60%, and the substrate 11, first film 13 and intermediate film 14 were heated to about 210° C.

In the first experiment, the quantity of gold with respect to the quantity of platinum was defined by an area ratio. The term "gold area ratio" was defined as the percentage of the total area of thin pieces of gold with respect to the whole area of a target of platinum used to fabricate second film 15 in accordance with the high frequency sputtering method.

The "gold area ratios" for the various tests performed in the first experiment are shown in Table 2 below.

TABLE 2

| | Film 15 | |
|---|---|---|
| Curve | Average film thickness (μ) | Gold area ratio (%) |
| a | 0.0003 | 0 |
| b | 0.0003 | 3.3 |
| c | 0.0003 | 5 |
| d | 0.0003 | 9.0 |
| e | 0 | — |

Figure 3:
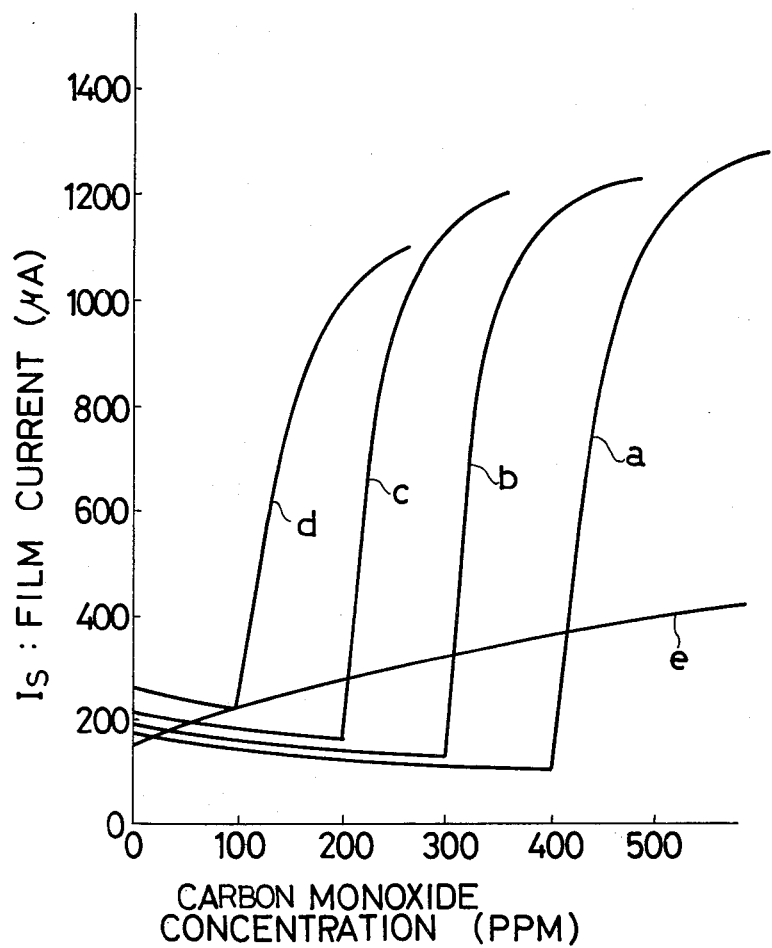
FIG. 3 is a graph plotting film current in $\mu A$ on the vertical axis versus carbon monoxide (CO) concentration in PPM on the horizontal axis of the characteristic curves produced by the first experiment.

FIG. 3 is a graph representation of the first experiment. FIG. 3 plots film current $I_S$ in μA on the vertical axis versus carbon monoxide concentration $C_M$ in PPM on the horizontal axis detected by carbon monoxide detecting element of the present invention having different gold area ratios for film 15. The ambient temperature, the ambient humidity, and the temperature of substrate 11, first film 13 and intermediate film 14 were maintained constant in the first experiment.

The characteristic curves a, b, c and d in FIG. 3 represent experiment results for gold area ratios of 0%, 3.3.%, 5% and 9.0%, respectively, as shown in Table 2 above. It is apparent from these characteristic curves a, b, c and d that as the quantity of gold is increased, the range of carbon monoxide concentration $C_M$ in which film current $I_S$ varies in a stepwise manner is shifted towards the low $C_M$ zone. It is also apparent that the range of carbon monoxide variation which produces the stepwise variation is also reduced.

According to additional experiments, it has been discovered that the film current $I_S$ makes a stepwise variation that can be electronically sensed, with a gold area ratio of up to about 50%. In addition, it is also discovered that if the platinum atom layer is varied in a range of 0.3 to 30, the carbon monoxide concentration $C_M$ range in which film current $I_S$ varies stepwise is substantially unaffected.

In addition, a carbon monoxide detecting device having no second film 15 was tested. These tests generated the characteristic curve e shown in FIG. 3. As is apparent from characteristic curve e, the film current $I_S$ does not exhibit the stepwise variation. It should be noted that the inventors are not in agreement as to the theoretical explanation for the stepwise film current $I_S$ produced by carbon monoxide detecting devices of the present invention having a second film 15 of platinum or, platinum and gold, formed on first and intermediate films 13, 14, respectively.

Figure 4:
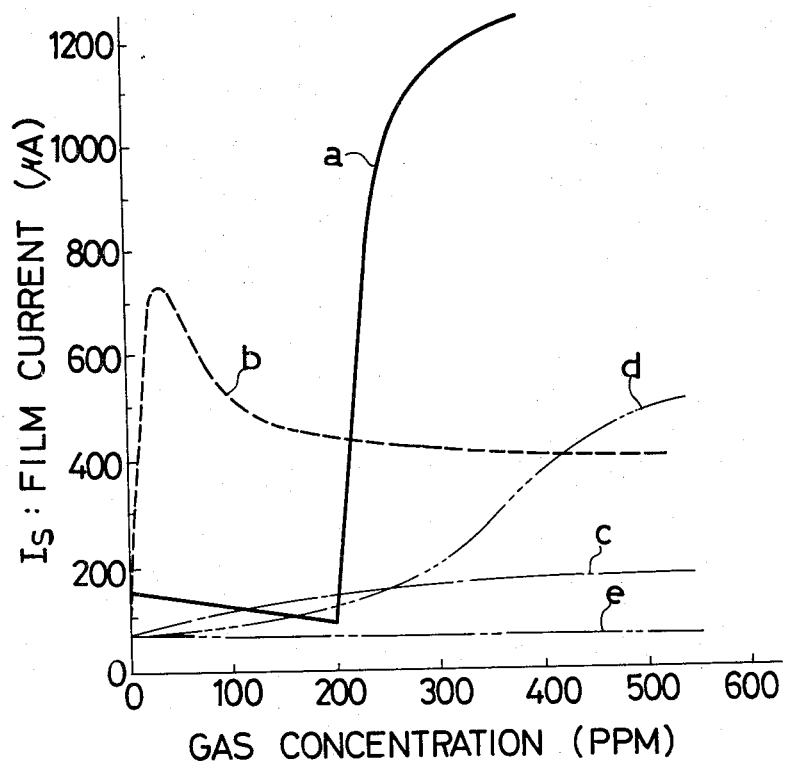
FIG. 4 is a graph plotting film current in $\mu A$ on the vertical axis versus gas concentration in PPM on the horizontal axis of the characteristic curves produced by the second experiment.

FIG. 4 is a graph representation plotting the characteristic curves generated by the second experiment in which the effects of various gases on the carbon monoxide detection response were investigated. FIG. 4 plots film current $I_S$ in $\mu A$ on the vertical axis versus gas concentration in PPM on the horizontal axis.

The heating temperature of the substrate 11 was about 210° C. in FIG. 4. The characteristic curves a, b, c, d and e in FIG. 4 plot the effect on the film currents $I_S$ caused by the gases of carbon monoxide (CO), ethylalcohol ($C_2H_5OH$), ethylene ($C_2H_4$), hydrogen ($H_2$), isobutane (iso—$C_4H_{10}$) or methane ($CH_4$), respectively.

As is apparent from FIG. 4, the carbon monoxide detecting element as employed in the present invention can detect ethylalcohol, even at the low gas concentration range.

It is assumed, for purposes of explanation, that a warning circuit responsive to the carbon monoxide detecting element as employed in the present invention is designed to change operational state when the film current $I_S$ of the carbon monoxide detecting element reaches about 600–1000 $\mu A$. This operational change of state corresponds to a concentration of carbon monoxide has reached about 200–300 PPM. However, in the situation where an ethylalcohol gas having a concentration about 50 PPM is present in a gas atmosphere having a carbon monoxide concentration of less than 200 PPM, the film current $I_S$ of the carbon monoxide detecting element will be greater than about 600 $\mu A$, causing the warning unit to change state and, thus, provide a false alarm because the carbon monoxide concentration level is less than the preselected danger level.

In order to avoid such a false alarm the threshold value of current of the warning unit for changing state is set to be higher than the peak current $I_S$ produced by the carbon monoxide detecting element with respect to ethylalcohol. As stated above, curve b indicates that this peak value of film current $I_S$ is less than 800 $\mu A$. However, the maximum desired carbon monoxide concentration occurs when the film current $I_S$ is 1000 $\mu A$. Thus, the warning unit must be able to sense accurately a film current $I_S$ value in the range of 800 $\mu A$ to 1000 $\mu A$ in order to provide a correct warning indication.

In order to overcome the high accuracy requirements of the warning unit, the present invention employs two separate carbon monoxide detecting elements. The first carbon monoxide detecting element is fabricated or is heated so as to produce a stepwise change in film current over a first preselected range in carbon monoxide concentration. In comparison, the second carbon monoxide detecting element is fabricated or heated so as to produce a stepwise change in film current over a second preselected range in carbon monoxide concentration. The first preselected range is made to be different from the second preselected range. The film current produced by the first carbon monoxide detecting element is compared in a comparing means with the film current produced by the second carbon monoxide detecting element, and the comparing means provides a difference voltage signal as an output, which is applied to the warning unit.

Figure 5:
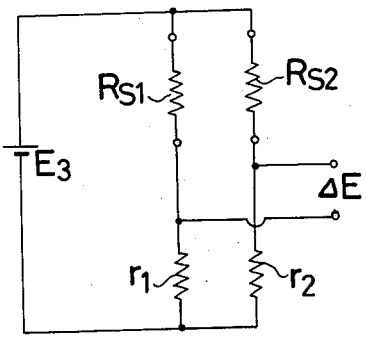
FIG. 5 shows a schematic block diagram of one embodiment of the present invention.

In a preferred embodiment of the present invention, the first and second carbon monoxide detecting elements are incorporated in a bridge circuit, as shown in FIG. 5.

For the detecting apparatus according to the present invention, the following carbon monoxide detecting element combinations are considered in detail below.

First Combination

The first and second carbon monoxide detecting elements are each fabricated by omitting the intermediate layer 14 and by forming the second layer 15 directly on the first layer 13.

Second Combination

The first carbon monoxide detecting element is fabricated by omitting the intermediate layer 14 and by forming the second layer 15 directly on the first layer 13.

The second carbon monoxide detecting element is fabricated so as to have a first film 13, an intermediate film 14, and a second film 15, as discussed above.

Third Combination

The first and second carbon monoxide detecting elements are fabricated so as each has a first film 13, an intermediate film 14, and a second film 15, as discussed above.

One embodiment of the present invention is now described in detail with reference to the relevant Figures.

FIG. 5 shows a circuit diagram of the embodiment of the present invention, in which two carbon monoxide detecting elements in accordance with the third combination discussed above are employed. Of course, carbon monoxide detecting elements in accordance with the first or second combination could be employed in lieu of the third combination, which is used only for purposes of explanation.

Referring to FIG. 5, reference characters $R_{S1}$ and $R_{S2}$ designate the film resistance of the first and second carbon monoxide detecting elements, respectively. The first carbon monoxide detecting element may be obtained by modifying the carbon monoxide detecting element shown in FIG. 1 so that the second film 15 is made only of platinum, i.e., the gold area ratio is zero. The second carbon monoxide detecting element may be obtained by modifying the carbon monoxide detecting element shown in FIG. 1 so that the second film 15 is made predominantly of platinum and has a gold area ratio of 5%. It should be noted that in FIG. 5, reference characters $r_1$ and $r_2$ designate fixed resistors, and reference character $E_3$ designates a driving electric source.

Figure 6:
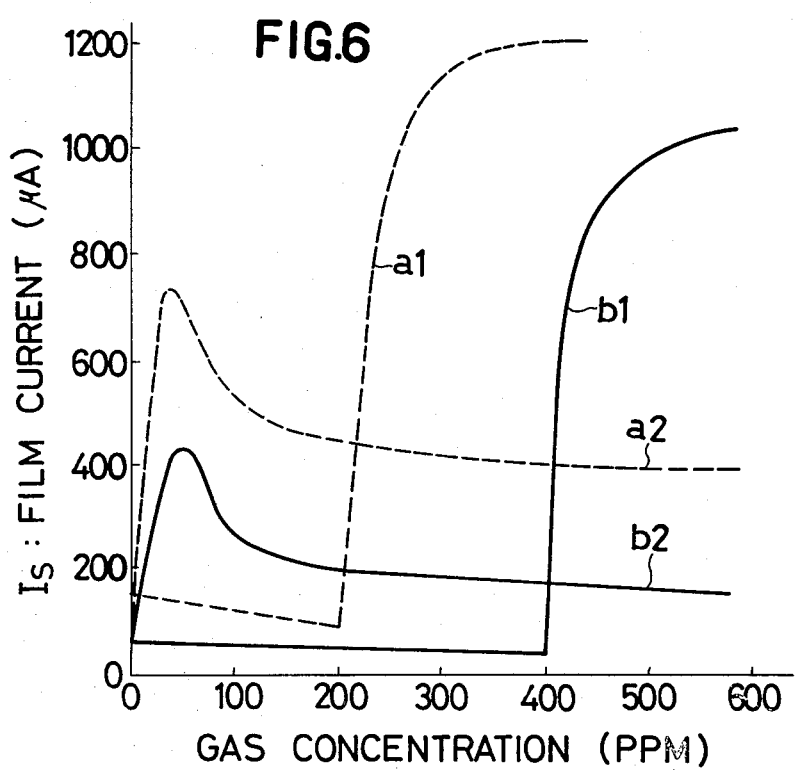
FIG. 6 is a graph plotting film current in $\mu A$ on the vertical axis versus gas concentration in PPM on the horizontal axis of the characteristic curves for carbon monoxide and ethyl alcohol produced by the first and second carbon monoxide detecting elements employed by the present invention.

FIG. 6 is a graph representation of the carbon monoxide and ethylalcohol detection responses of the first and second carbon monoxide detecting elements employed by the embodiment of the present invention. FIG. 6 plots film current $I_S$ in $\mu A$ on the vertical axis versus gas concentration in PPM on the horizontal axis detected by the first and second carbon monoxide detecting elements. Characteristic curves a1 and a2 represent the carbon monoxide and ethylalcohol responses, respectively, of the first carbon monoxide detecting element that is employed in the embodiment. Characteristic curves b1 and b2 represent the carbon monoxide and ethylalcohol detection responses, respectively, of the second carbon monoxide detecting element that is employed in the embodiment. Curves a1 and a2 are not coincident with curves b1 and b2 because the second film 15 of the first carbon monoxide detecting element has a higher gold area ratio than does the second film 15 of the second carbon monoxide detecting element.

As shown in FIG. 6, the first carbon monoxide detecting element exhibits a stepwise change in film current when the concentration of carbon monoxide reaches about 200 PPM, whereas the second carbon monoxide detecting element exhibits a stepwise change in film current when the concentration of carbon monoxide reaches about 400 PPM. However, with respect to detection of ethylalcohol, the first carbon monoxide detecting element and the second carbon monoxide detecting element have substantially equivalent detection characteristics; the only difference therebetween is that the film current of the second carbon monoxide detecting element is somewhat smaller than that of the first carbon monoxide detecting element.

Figure 7:
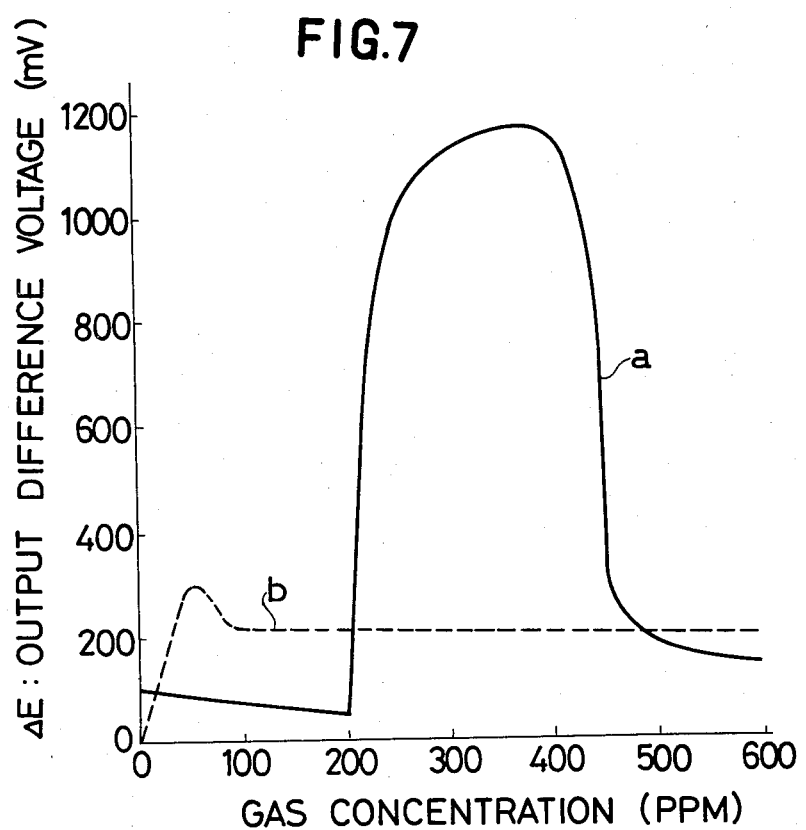
FIG. 7 is a graph plotting the output difference voltage $\Delta E$ in mV on the vertical axis versus gas concentration in PPM on the horizontal axis of the carbon monoxide detection response of the carbon monoxide detecting apparatus of the present invention.

Thus, if the two carbon monoxide detecting elements having different carbon monoxide detection concentration ranges are incorporated in the comparing means of the present invention, such as of FIG. 5, the bridge circuit provides an output difference voltage ΔE, as plotted in FIG. 7. FIG. 7 plots the output difference voltage ΔE in mV on the vertical axis versus gas concentration in PPM on the horizontal axis. Curve a of FIG. 7 represents the difference voltage ΔE between the carbon monoxide detection curves a1 and b1 of FIG. 6, and curve b of FIG. 7 represents the difference voltage ΔE between the ethylalcohol detection curves a2 and b2 of FIG. 6.

As is apparent from FIG. 7, with respect to carbon monoxide, the output difference voltage ΔE is a signal whose value is in proportion to the characteristic curve a1 of FIG. 6 in the range of 0–400 PPM, but with respect to ethylalcohol, it is a signal whose value is proportional to the difference between the characteristic curve a2 and b2 of FIG. 6 in the same range of 0–400 PPM. Therefore, in the present invention where two carbon monoxide detecting elements are employed, the peak value of the ethylalcohol output signal is much smaller than that of the carbon monoxide output signal, as compared to the case when only one carbon monoxide detecting element is employed. Accordingly, in the carbon monoxide detecting apparatus of the present invention, the range of the bridge circuit output difference voltage ΔE in the concentration range of carbon monoxide to be detected is increased considerably. Therefore, the warning circuit may exhibit a low accuracy and yet still produce the desired warning response when the carbon monoxide detecting apparatus of the present invention is employed. Therefore, the construction of the warning circuit can be simplified.

As described above, the first method used to provide the desired carbon monoxide detection response of the carbon monoxide detecting apparatus of the present invention was to fabricate differently the two carbon monoxide elements employed in the apparatus. However, a second method to provide the desired carbon monoxide detection response of the carbon monoxide detecting apparatus of the present invention is now described.

As discussed above with respect to FIGS. 1A and 1B, a heating resistor is provided for the carbon monoxide detecting element on the second side of substrate 11 between the heating electrodes 25 and 27. In the third experiment of the present invention, the effect of the heating temperature parameter T with respect to carbon monoxide response for a carbon monoxide detecting element having a second film 15 with a gold area ratio of 5% was measured for the temperatures T shown in Table 3 below.

TABLE 3

| (Curve) | Heating Temperature T (°C.) |
|---|---|
| a | 220 |
| b | 210 |
| c | 200 |
| d | 190 |
| e | 170 |

Figure 8:
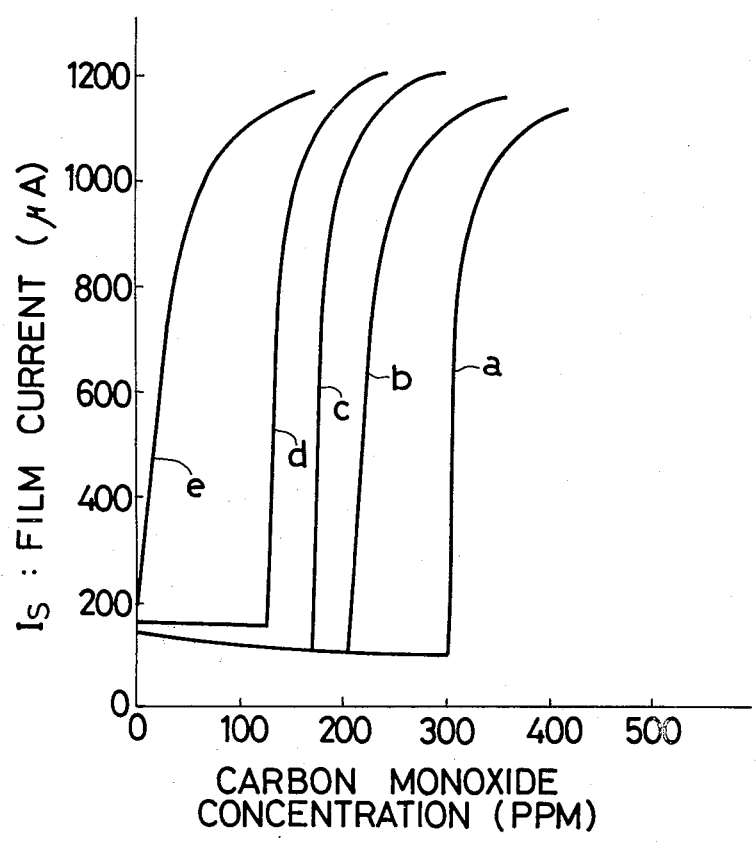
FIG. 8 is a graph plotting film current in $\mu A$ on the vertical axis versus carbon monoxide concentration in PPM on the horizontal axis of the characteristic curves produced by the third experiment.

FIG. 8 is a graph representation plotting the characteristic curves a to e generated by the third experiment in which the effect of heating temperature T of the carbon monoxide detecting element was investigated. FIG. 8 plots film current $I_S$ in μA on the vertical axis versus carbon monoxide concentration $C_M$ is PPM on the horizontal axis.

It is apparent from FIG. 8 that the carbon monoxide concentration $C_M$ range which produces the stepwise change in the film current $I_S$ is changed in accordance with the heating temperature T, and is increased as the heating temperature T is increased.

Thus, as is apparent from FIG. 8, the concentration of carbon monoxide which changes the film current stepwise can be selected by changing the heating temperature of the carbon monoxide detecting element. If in the third combination of the present invention the first carbon monoxide detecting element is heated to about 220° C. and the second carbon monoxide detecting element is heated to about 210° C., a carbon monoxide having a concentration of about 200 PPM or greater can be detected by the present invention. The use of different temperatures also applies to the first and second combinations of the present invention, as discussed above.

In the fourth experiment of the present invention, the effect of the platinum amount in the intermediate film 14 with respect to carbon monoxide response for a carbon monoxide detecting element was measured. The term "Pt area ratio" means the percentage value of the area occupied by the thin pieces of platinum with respect to the tin target used in manufacturing the intermediate film 14. Similarly, the term "Sb area ratio" means the percentage value of the area occupied by the thin pieces of antimony with respect to the tin target used in manufacturing the first film 13. The values of the Pt area ratio used in the fourth experiment are shown in Table 4 below.

TABLE 4

| | Film 13 | | Film 14 | | Film 15 | |
|---|---|---|---|---|---|---|
| Curve | Thickness | Sb area ratio | Thickness | Pt area ratio | Average thickness | Gold area ratio |
| a | 0.06 μm | 4% | 0.06 μm | 4.6% | 0.0003 μm | 5% |
| b | 0.06 μm | 4% | 0.06 μm | 1.6% | 0.0003 μm | 5% |
| c | 0.06 μm | 4% | 0 | — | 0.0003 μm | 5% |

Figure 9:
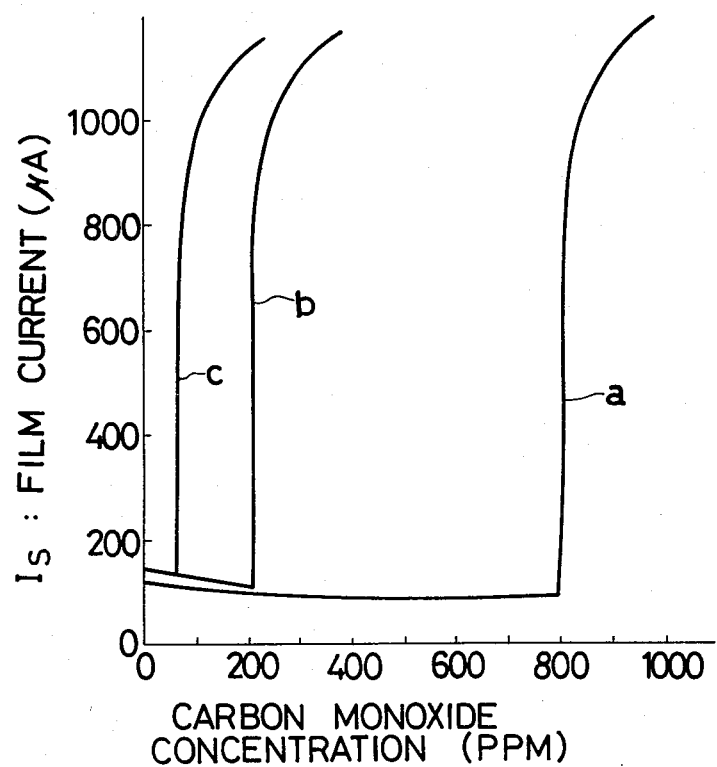
FIG. 9 is a graph plotting film current in $\mu A$ on the vertical axis versus carbon monoxide concentration in PPM on the horizontal axis of the characteristic curves versus produced by the fourth experiment.

FIG. 9 is a graph representation plotting the characteristic curves a to c generated by the fourth experiment in which the effect of the Pt area ratio of the intermediate film 14 of the carbon monoxide detecting element was investigated. FIG. 9 plots film current $I_S$ in μA on the vertical axis versus carbon monoxide concentration $C_M$ in PPM on the horizontal axis.

Figure 10:
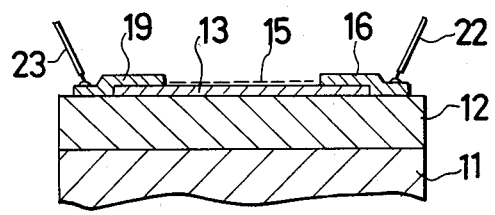
FIG. 10 shows a cross-sectional view of another embodiment of the carbon monoxide detecting element as employed by the carbon monoxide detecting apparatus of the present invention.

As is apparent from FIG. 9, the concentration of carbon monoxide which changes the film current of the detecting element stepwise can be varied by varying the platinum amount in the intermediate film 14. This can be also applied to the above described second and third combinations. In addition, the carbon monoxide detecting element exhibits a stepwise change in film current over a preselected range in carbon monoxide concentration even when the intermediate film 14 is omitted. FIG. 10 is a cross-sectional side view of a carbon monoxide detecting element which does not have an intermediate film 14. Experiments have shown that with respect to the carbon monoxide detecting element of FIG. 10, the stepwise change in film current over a preselected range in carbon monoxide can be varied by changing the temperature T or the gold area ratio of second film 15.

The various methods and combinations for making the two carbon monoxide detecting elements, as employed in the carbon monoxide detecting apparatus of the present invention, exhibiting stepwise changes in film current over separate preselected ranges in carbon monoxide concentration, are shown in Table 5 below.

Methods of making the first and second concentration values of carbon monoxide, which vary the film current of the first and second detection elements stepwise, different from each other are collectively indicated in Table 5 below. In Table 5, the symbol (o) in the heating temperature column indicates that the heating temperature of the first carbon monoxide detecting element is equal to that of the second carbon monoxide detecting element, and the symbol (x) indicates that the heating temperature of the first carbon monoxide detecting element is different from that of the second carbon monoxide detecting element. In the second combination, the symbol (Δ) indicates that the intermediate film 14 is removed from one of the first or second carbon monoxide detecting element, respectively.

TABLE 5

| Combination | First Combination | | | Second Combination | | | | | Third Combination | | | | | |
|---|---|---|---|---|---|---|---|---|---|---|---|---|---|---|
| | | | | | | | | Example | | | | | | |
| Parameter | 1 | 2 | 3 | 4 | 5 | 6 | 7 | 8 | 9 | 10 | 11 | 12 | 13 | 14 |
| Heating temperature | x | o | x | x | o | x | o | o | o | x | o | x | x | x |
| Platinum area ratio | — | — | — | Δ | Δ | Δ | Δ | o | x | o | x | x | o | x |
| Gold area ratio | o | x | x | o | x | x | o | x | o | o | x | o | x | x |

As is apparent from the above description, a difference signal ΔE between the signal proportional to the film current of the first carbon monoxide detecting element, which varies stepwise at a first concentration value of carbon monoxide, and the signal proportional to the film current of the second carbon monoxide detecting element, which varies stepwise at a second concentration value of carbon monoxide, is obtained by the carbon monoxide detecting apparatus of the present invention. Accordingly, it is possible in the present invention to make the detection signal caused by a coexisting gas such as ethylalcohol gas to be much smaller than the signal caused by the detection of carbon monoxide gas. Therefore, in the present invention, it is possible to minimize the effect of coexisting gases, which leads to simplification of the construction of a warning circuit.

In addition, in the case where two carbon monoxide detecting elements employed in the present invention have equal heating temperatures, the two carbon monoxide detecting elements can be formed on one substrate. In this case, only one heating resistor is needed.

What is claimed:

1. A carbon monoxide gas detecting apparatus adjusted to respond to a preselected range of carbon monoxide gas concentrations and comprising:

(a) a first carbon monoxide gas detecting element means having an insulating substrate, a first film predominantly of stannic oxide and a donor selected from the group consisting of antimony and bismuth formed on said insulating substrate, an intermediate film predominately of stannic oxide and an acceptor selected from the group consisting of platinum, aluminum and boron formed on said first film, and a second film predominately of platinum formed on said intermediate film, for producing a stepwise change in a first film current at a first preselected carbon monoxide gas concentration;

(b) a second carbon monoxide gas detecting element means having an insulating substrate, a first film predominantly of stannic oxide and a donor selected from the group consisting of antimony and bismuth formed on said insulating substrate, an intermediate film predominately of stannic oxide and an acceptor selected from the group consisting of platinum, aluminum and boron formed on said first film, and a second film predominately of platinum formed on said intermediate film, for producing a stepwise change in a second film current at a second preselected carbon monoxide gas concentration different from the carbon monoxide gas concentration at which the first detecting element responds in a stepwise manner; and, (c) comparing means responsive to said first and second film currents for providing a difference voltage signal having an amplitude which varies in response to the absolute value of the difference between said first film current and said second film current.

2. The carbon monoxide detecting apparatus as recited in claim 1, wherein said comparing means is bridge circuit.

3. The carbon monoxide detecting apparatus as recited in claim 1, wherein gold is added to said second film of said first carbon monoxide detecting element means.

4. The carbon monoxide detecting apparatus as recited in claim 3, wherein gold is added to said second film of said second carbon monoxide detecting element means.

5. The carbon monoxide detecting apparatus as recited in claim 4, wherein the temperature of said first insulating substrate of said first carbon monoxide detecting element means is different from the temperature of said second insulating substrate of said second carbon monoxide detecting element means.

6. The carbon monoxide detecting apparatus as recited in claim 1, wherein the temperature of said first insulating substrate of said first carbon monoxide detecting element means is different from the temperature of said second insulating substrate of said second carbon monoxide detecting element means.

* * * * *